US010107270B2

(12) United States Patent
Marion, III et al.

(10) Patent No.: US 10,107,270 B2
(45) Date of Patent: Oct. 23, 2018

(54) BIDIRECTIONAL SHAPE MEMORY DEVICE

(71) Applicant: LAWRENCE LIVERMORE NATIONAL SECURITY, LLC, Livemore, CA (US)

(72) Inventors: John E. Marion, III, Livemore, CA (US); Jane P. Bearinger, Livermore, CA (US); Thomas S. Wilson, San Leandro, CA (US); Ward Small, IV, Livemore, CA (US); Duncan J. Maitland, College Station, TX (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 281 days.

(21) Appl. No.: 15/053,293

(22) Filed: Feb. 25, 2016

(65) Prior Publication Data

US 2016/0177929 A1 Jun. 23, 2016

Related U.S. Application Data

(62) Division of application No. 13/829,670, filed on Mar. 14, 2013.

(51) Int. Cl.
*F03G 6/06* (2006.01)
*F03G 7/06* (2006.01)
(Continued)

(52) U.S. Cl.
CPC .......... *F03G 7/065* (2013.01); *A61B 17/3207* (2013.01); *A61B 17/320725* (2013.01);
(Continued)

(58) Field of Classification Search
CPC ........ A61B 17/3207; A61B 17/320725; A61B 2017/00867; A61B 2017/22084;
(Continued)

(56) References Cited

U.S. PATENT DOCUMENTS

| | | | |
|---|---|---|---|
| 5,749,894 | A | 5/1998 | Engelson |
| 6,059,815 | A | 5/2000 | Lee et al. |

(Continued)

OTHER PUBLICATIONS

Small, IV, "Prototype Fabrication and Preliminary in Vitro Testing of a Shape Memory Endovascular Thrombectomy Device," IEEE Trans. on Biomedical Eng., vol. 54, No. 9, 2007, pp. 1657-1666.

*Primary Examiner* — Jocelin Tanner
(74) *Attorney, Agent, or Firm* — Eddie E. Scott

(57) ABSTRACT

A resistively heated shape memory polymer device is operated using resistive heating to heat the shape memory polymer device. The resistively heated shape memory polymer device is made by providing a wire that includes a resistive medium. The wire is coated with a first shape memory polymer. The wire is exposed and electrical leads are attached to the wire. In one embodiment the shape memory polymer device is in the form of a clot destruction device. In another embodiment the shape memory polymer device is in the form of a microvalve. In another embodiment the shape memory polymer device is in the form of a micropump. In yet another embodiment the shape memory polymer device is in the form of a thermostat or relay switch.

1 Claim, 8 Drawing Sheets

(51) Int. Cl.

| | |
|---|---|
| ***A61B 17/3207*** | (2006.01) |
| ***F16K 99/00*** | (2006.01) |
| ***F16K 31/02*** | (2006.01) |
| ***H01H 37/32*** | (2006.01) |
| ***H01H 37/46*** | (2006.01) |
| *A61B 17/00* | (2006.01) |
| *A61B 17/22* | (2006.01) |

(52) U.S. Cl.

CPC ........ *F16K 31/025* (2013.01); *F16K 99/0005* (2013.01); *F16K 99/0038* (2013.01); *F16K 99/0044* (2013.01); *H01H 37/323* (2013.01); *H01H 37/46* (2013.01); *A61B 2017/00867* (2013.01); *A61B 2017/22084* (2013.01); *A61B 2017/22094* (2013.01); *H01H 2205/002* (2013.01)

(58) Field of Classification Search

CPC ......... A61B 2017/22094; F04B 19/006; F04B 43/043; F04B 43/095; F16K 99/0001; F16K 99/0038; F16K 99/0005; F16K 99/0044; F03G 7/065; H01H 37/323; H01H 37/46; H01H 2205/002

See application file for complete search history.

(56) References Cited

U.S. PATENT DOCUMENTS

| | | | |
|---|---|---|---|
| 6,102,917 A | 8/2000 | Maitland et al. | |
| 6,160,084 A | 12/2000 | Langer et al. | |
| 6,388,043 B1 | 5/2002 | Langer et al. | |
| 6,418,252 B1 | 7/2002 | Maitland et al. | |
| 6,740,094 B2 | 5/2004 | Maitland et al. | |
| 7,386,203 B2 | 6/2008 | Maitland et al. | |
| 7,744,604 B2 | 6/2010 | Maitland et al. | |
| 2002/0010415 A1 | 1/2002 | Simon | |
| 2004/0034363 A1 | 2/2004 | Wilson | |
| 2004/0115067 A1* | 6/2004 | Rush ................ | A61M 5/14216 417/322 |
| 2006/0009785 A1* | 1/2006 | Maitland ............. | A61B 17/221 606/113 |
| 2006/0122621 A1 | 6/2006 | Truckai | |
| 2011/0015613 A1 | 1/2011 | Anzai | |

* cited by examiner

BIDIRECTIONAL SHAPE MEMORY DEVICE

CROSS-REFERENCE TO RELATED APPLICATIONS

The present application is a Division of application Ser. No. 13/829,670 filed Mar. 14, 2013, entitled "Bidirectional Shape Memory Device", the disclosure of which is hereby incorporated by reference in its entirety for all purposes.

STATEMENT AS TO RIGHTS TO INVENTIONS MADE UNDER FEDERALLY SPONSORED RESEARCH AND DEVELOPMENT

The United States Government has rights in this invention pursuant to Contract No. DE-AC52-07NA27344 between the United States Department of Energy and Lawrence Livermore National Security, LLC for the operation of Lawrence Livermore National Laboratory.

BACKGROUND

Field of Endeavor

The present invention relates to shape memory devices and more particularly to a bidirectional shape memory device.

State of Technology

Shape-memory materials have the useful ability of being formable into a primary shape, being reformable into a stable secondary shape, and then being controllably actuated to recover their primary shape. Both metal alloys and polymeric materials can have shape memory. In the case of metals, the shape-memory effect arises from thermally induced solid phase transformations in which the lattice structure of the atoms changes, resulting in macroscopic changes in modulus and dimensions. In the case of polymeric materials, the primary shape is obtained after processing and fixed by physical structures or chemical crosslinking. The secondary shape is obtained by deforming the material while is an elastomeric state and that shape is fixed in one of several ways including cooling the polymer below a crystalline, liquid crystalline, or glass transition temperature; by inducing additional covalent or ionic crosslinking, etc. While in the secondary shape some or all of the polymer chains are perturbed from their equilibrium random walk conformation, having a certain degree of bulk orientation. The oriented chains have a certain potential energy, due to their decreased entropy, which provides the driving force for the shape recovery. However, they do not spontaneously recovery due to either kinetic effects (if below their lower Tg) or physical restraints (physical or chemical crosslinks). Actuation then occurs for the recovery to the primary shape by removing that restraint, e.g. heating the polymer above its glass transition or melting temperature removing ionic or covalent crosslinks, etc. However, devices made from shape memory polymer are only able to recover in one direction, i.e. they can go from any shape back to their original shape, but have to be manually forced back to any other shape.

Types of Shape Memory Polymer

Thermoplastic SMPs—thermoplastic polymers are those which can be heated into a melt state in which all prior solid shape memory has been lost, processed into a shape, and solidified. If need be they can be re-heated to their melt state and re-processed a number of times. In thermoplastic SMPs, the shape memory effect generally relates to the material having a multiphase structure in which the different phases have different thermal transitions, which may be due to glass transitions, crystalline melting points, liquid crystal-solid transitions, ionomeric transitions, etc. The primary shape is obtained by processing in the melt state above the highest transition temperature and then cooling to a temperature in which either a hard phase or other physical crosslink is formed to lock in that shape. The secondary shape is obtained by bringing the material to a temperature above its actuation temperature but below its melting temperature, mechanically shaping the material into its secondary shape, then cooling it below its actuation temperature. Suitable thermoplastic SMPs include block copolymers (linear di, tri, and multiblocks; alternating graft), immiscible polymer blends (neat and with coupling agents such as di or tri-block copolymers), semi-crystalline polymers, and linear polymers with ionomeric groups along the chain or grafted to the chain.

Thermosetting SMPs—thermosetting polymers are those which are processed into a part and simultaneously chemically crosslinked, so that the part is essentially one macromolecule. They cannot be re-processed by melting. In thermosetting SMPs the primary shape is obtained during the initial processing step involving crosslinking. The secondary shape is obtained by mechanically reshaping the material at a temperature or condition in which the material is in an elastomeric state. This secondary shape is locked in by cooling the material below the actuation temperature, which relates to a transition as described above. Suitable thermosetting SMPs include all of the types of materials described under thermoplastic SMPs but which can also be chemically crosslinked to form the primary shape. In addition, crosslinked homopolymers can also be used as SMPs with the actuation temperature typically being the glass transition temperature of the material.

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

This present invention provides a resistively heated shape memory polymer device. The device is operated using resistive heating to heat the shape memory polymer device. The resistively heated shape memory polymer device is made by providing a wire that includes a resistive medium. The wire is coated with a first shape memory polymer. The wire is exposed and electrical leads are attached to the wire. In one embodiment the shape memory polymer device is in the form of a clot destruction device. In another embodiment the shape memory polymer device is in the form of a microvalve. In another embodiment the shape memory polymer device is in the form of a micropump. In yet another embodiment the shape memory polymer device is in the form of a thermostat or relay switch.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF SPECIFIC EMBODIMENTS

Figures 1A, 1B, 1C, 1D:
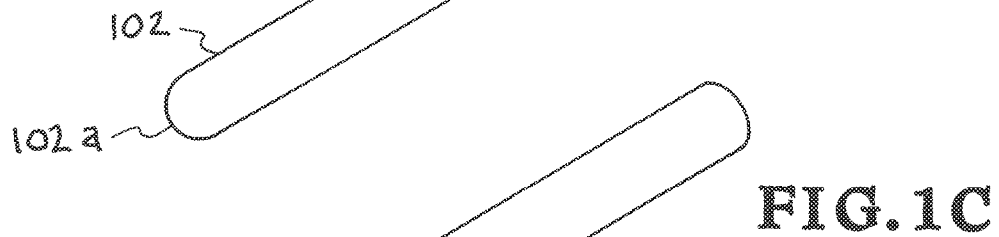
FIGS. 1A through 1D illustrate the forming of a wire of conductive shape memory polymer coil.

Referring to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Referring now to FIGS. 1A through 1D, one embodiment of a bidirectional shape memory device of the present invention and the making of the bidirectional shape memory device of the present invention are illustrated. Referring to FIG. 1A, a thermoresistive wire 100 is illustrated. The wire 100 is be made suitable resistive wire or is made of a composite. For example, the wire 100 can be made of resistive wire material, including but not limited to Ni—Cr alloy wire. The wire 100 may have a small spring constant. The wire 100 may expand upon heating.

Referring now to FIG. 1B, the wire 100 is coated with Shape Memory Polymer (SMP) 102. This provides a wire 100 embedded in shape memory polymer (SMP). The wire 100 can be coated by various coating process including dip coating, spray coating, deposition coating, and other forms of coating.

Referring now to FIGS. 1B and 1C, the ends 102A and 102B of the SMP 102 coating are cut off to expose the wire 100. Referring now to FIG. 1D, wire leads 104 and 106 are attached to the exposed wire 100. The wire lead 104 is attached to one end of the wire 100. The wire lead 106 is attached to the other end of the wire 100. This provides a thermoresistive wire coated with SMP which can be reprogrammed into other shapes such as a coil shapes or other shapes.

The present invention is further described and illustrated by a number of examples of systems constructed in accordance with the present invention. Various changes and modifications of these examples will be apparent to those skilled in the art from the description of the examples and by practice of the invention. The scope of the invention is not intended to be limited to the particular examples disclosed and the invention covers all modifications, equivalents, and alternatives falling within the spirit and scope of the invention as defined by the claims.

Example 1—Clot Destruction Device

The clot destruction device, in a preferred embodiment, consists of the lesser wire coil embedded in a greater SMP coil. The device would be straightened into a rod shape and pushed into the clot using a catheter system. Once in the clot, the device would be activated by applying a current to the wire. By varying the current, the coil contracts and expands thereby destroying the clot.

Figure 2:
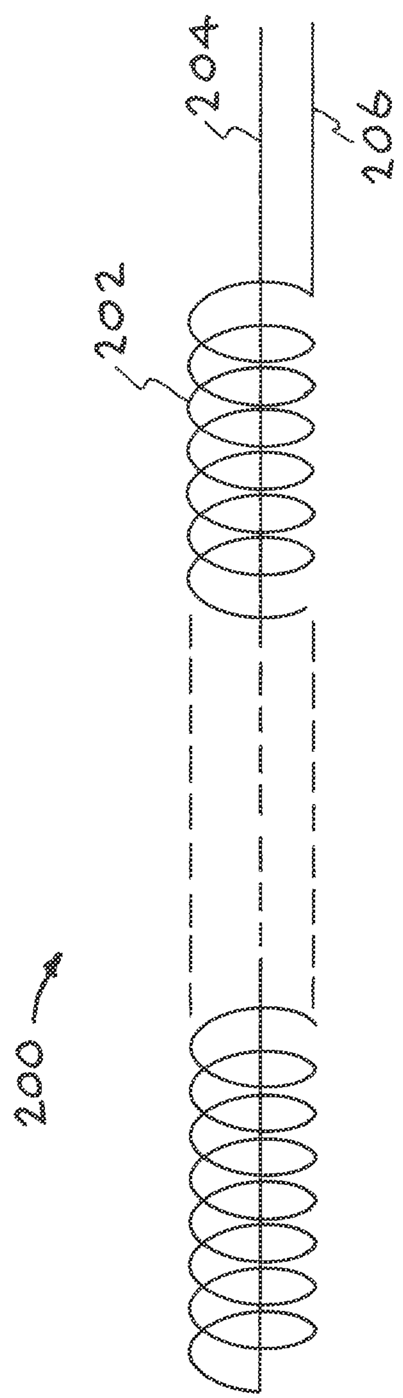
FIG. 2 illustrates one embodiment of a shape memory polymer coil of the present invention.

Referring now to FIG. 2, a clot destruction device is illustrated. The clot destruction device is designated generally by the reference numeral 200. The clot destruction device 200 is constructed as described in connection with FIGS. 1A-1D. The clot destruction device 200 includes a coil body portion 202 and leads 204 and 206.

In a preferred embodiment, the clot destruction device 200 provides a wire coil embedded in shape memory polymer to provide coil 202. The clot destruction device 200 is pushed into the clot using a catheter system. Once in the clot, the clot destruction device 200 is activated by applying a current to the wire leads 204 and 206. By varying the current the coil contracts and expands thereby destroying the clot. This, in combination with antithrombotic drugs could be effective in treating ischemic stroke.

Figure 3A:
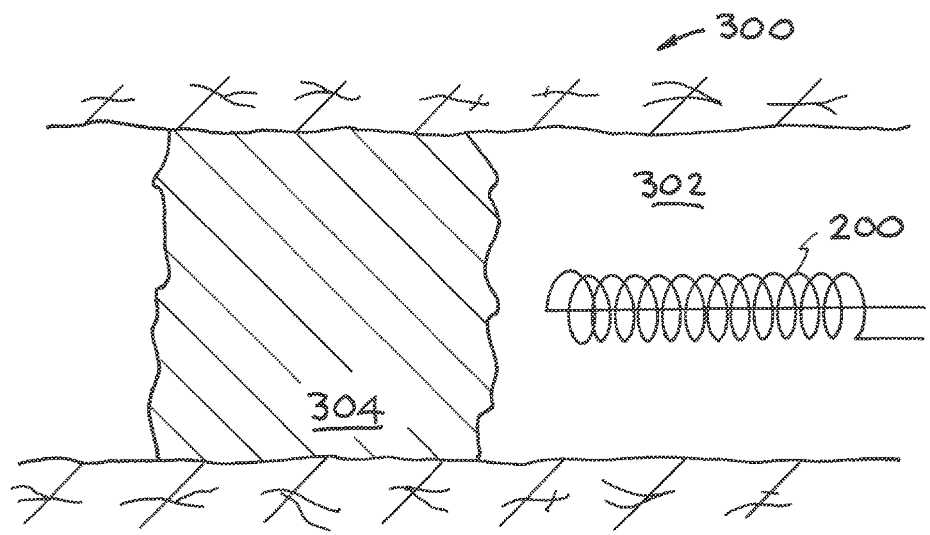
FIGS. 3A through 3E that illustrate the construction and operation of the shape memory polymer coil used as a clot destruction device.

Referring now to FIGS. 3A through 3E, a clot destruction device of the present invention is illustrated. The clot destruction device is designated generally by the reference numeral 300. Referring to FIG. 3A, the device 200 is introduced into the artery 302 at the site of the clot 304.

Figure 3B:
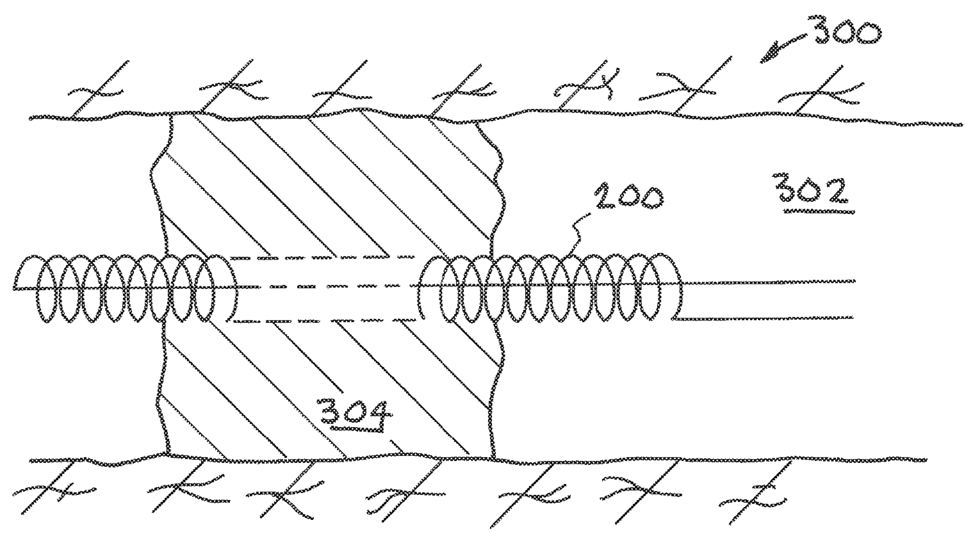
Figure 3C:
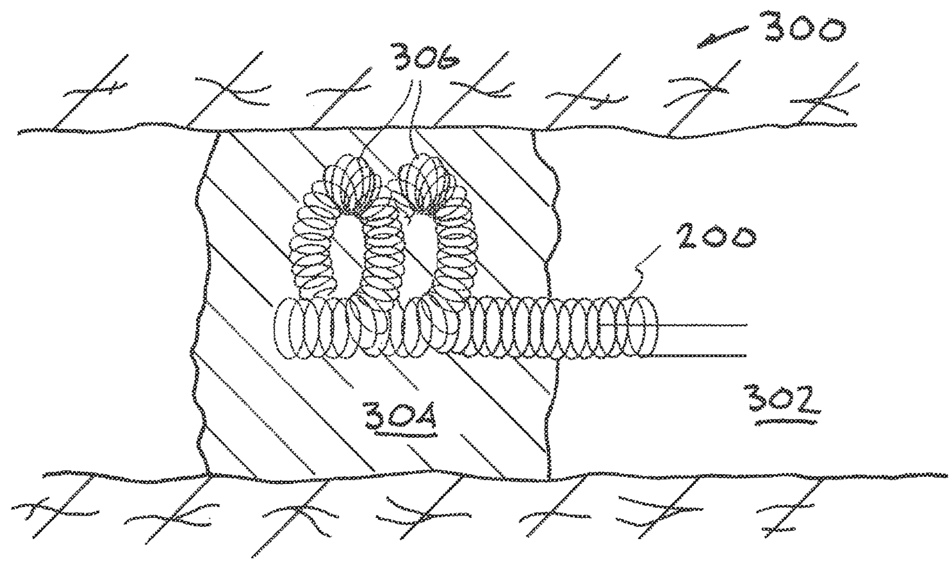

Referring now to FIG. 3B, the clot destruction device 300 is pushed through the clot 304. The coil 200 extends through the clot 304. Referring to FIG. 3C, current is passed through the wire of the coil 200, causing the coil 200 to contract producing the loops 306 of the coil 200.

Figure 3D:
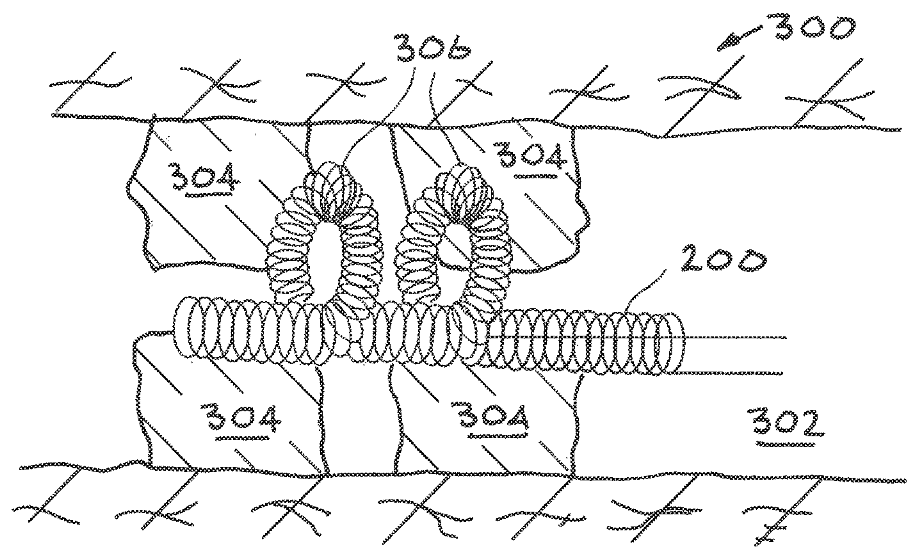
Figure 3E:
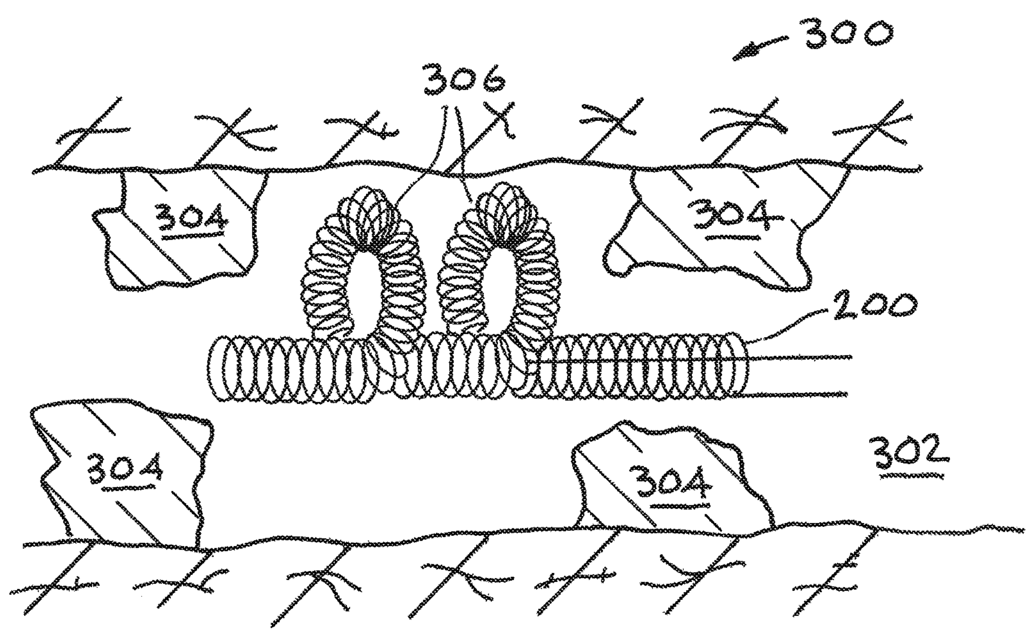

Referring now to FIGS. 3D and 3E, the clot destruction device 300 is turned on and off causing the current to alternatingly be passed through the wire of the coil 200, causing the coil 200 and the loops 306 to contract and expand. As illustrated in FIG. 3E, the clot 304 is in pieces and is virtually destroyed. This, in combination with antithrombotic drugs could be effective in treating ischemic stroke.

Example 2—Microvalve

Figure 4A:
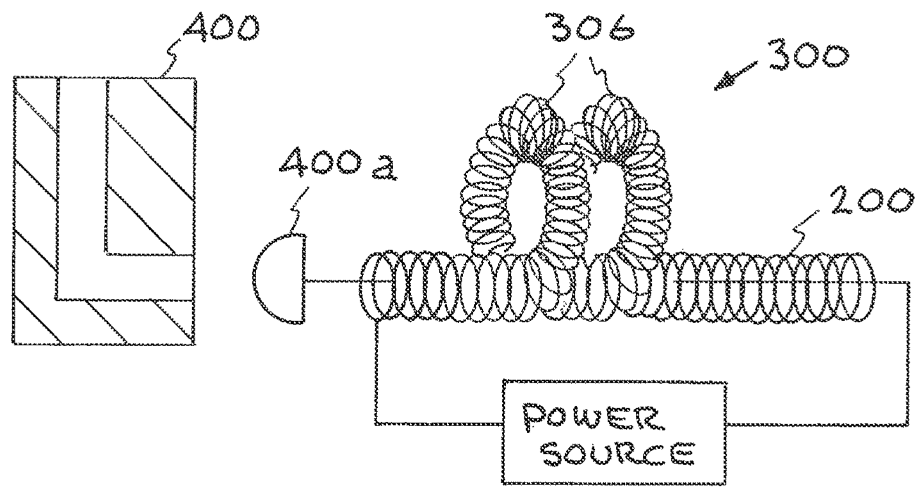
FIGS. 4A and 4B illustrated the construction and operation of the shape memory polymer coil constructed in accordance with FIGS. 1A-1D and illustrated in FIG. 2 used as a microvalve.

Referring now to FIGS. 4A and 3B the device 300 illustrated in FIGS. 3A-3E can perform as a microvalve. The microvalve consists of a wire embedded in shape memory polymer to provide the coil 200. The end of the coil 200 is oriented such that it plugs or opens the valve 400. When current passes through the wire, the coil 200 it opens the valve 200.

Figure 4B:
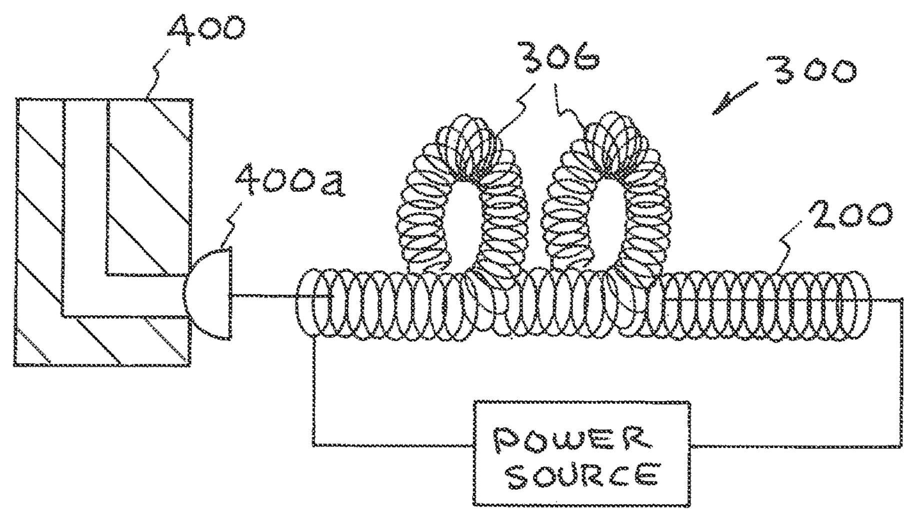

Referring now to FIG. 4B, no current through wire of the coil 200 plugs and closing microvalve 400. A plunger 400A is moved by the coil 200. Referring now to FIG. 4A, current running through wire of the coil 200 causes contracting of the coil 200 opening microvalve 400.

Example 3—Micropump

Figure 5A:
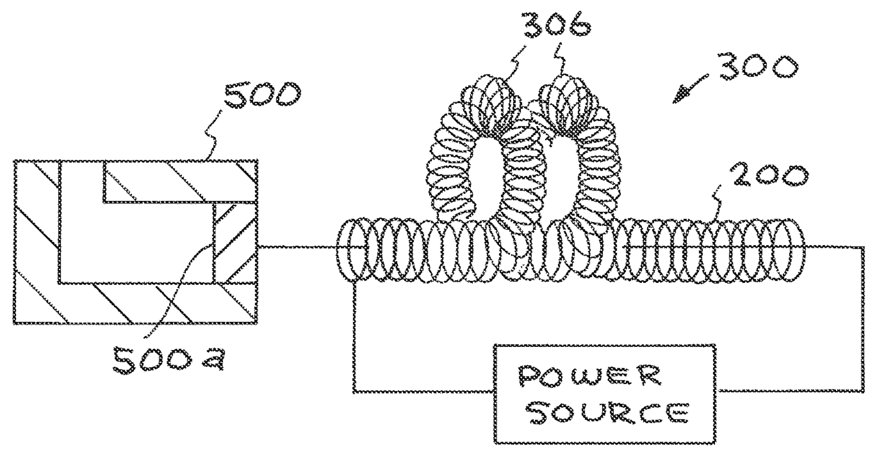
FIGS. 5A and 5B illustrated the construction and operation of the shape memory polymer coil constructed in accordance with FIGS. 1A-1D and illustrated in FIG. 2 used as a micropump.
Figure 5B:
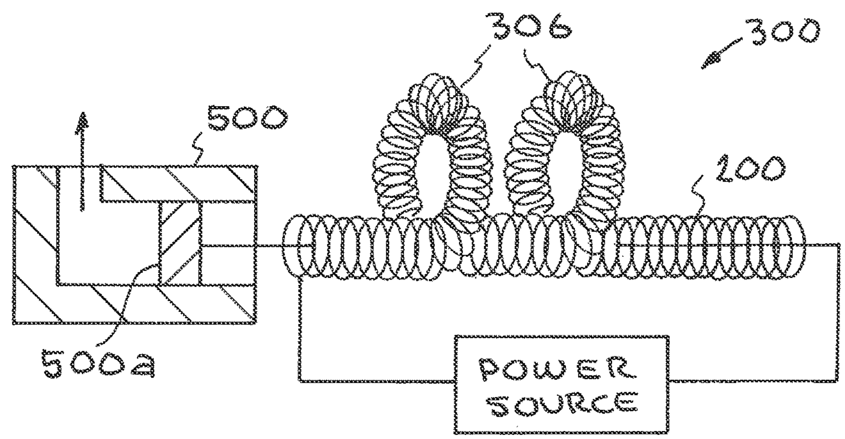

Referring now to FIGS. 5A and 5B the device 300 illustrated in FIGS. 3A-3E can perform as a micropump 500. The micropump 500 consists of a wire embedded in shape memory polymer to provide the coil 200. The end of the coil 200 is oriented such that it moves the cylinder 500*a* of the micropump 500. When current passes through the wire, the coil 200 it moves the cylinder 500*a*.

Referring now to FIG. 5B, no current through wire of the coil 200 moves the cylinder 500*a* of the micropump 500. Referring now to FIG. 5A, current running through wire of the coil 200 causes contracting of the coil 200 moving the cylinder 500*a* of the micropump 500.

Example 4—Thermostat and Relay Switch

Figure 6A:
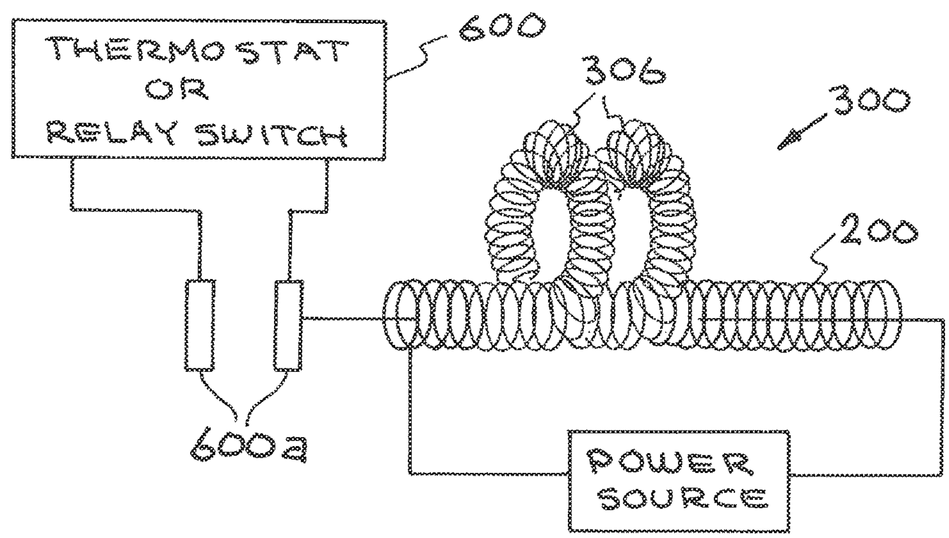
FIGS. 6A and 6B illustrated the construction and operation of the shape memory polymer coil constructed in accordance with FIGS. 1A-1D and illustrated in FIG. 2 used as a thermostat and relay switch.
Figure 6B:
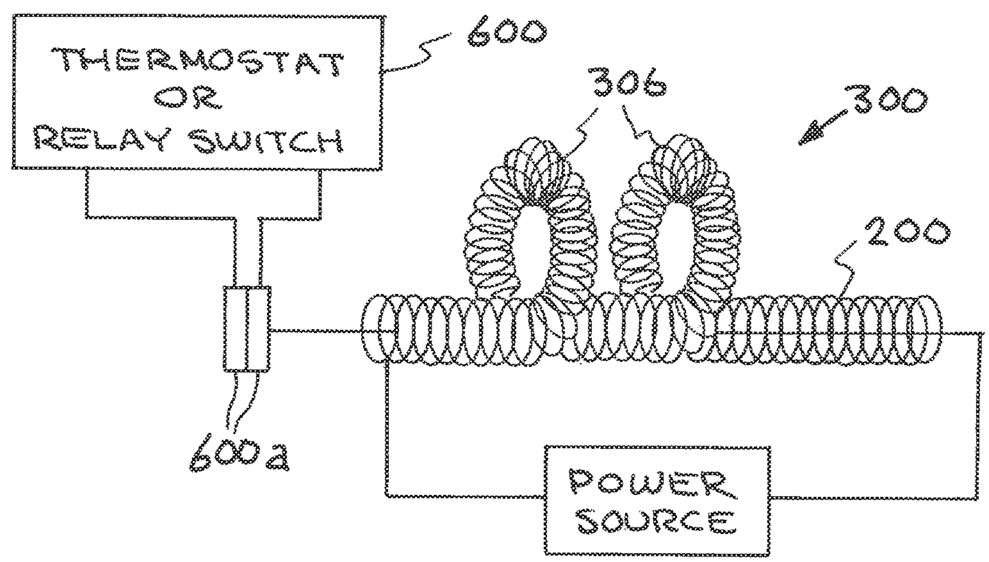

Referring now to FIGS. 6A and 6B the device 300 illustrated in FIGS. 3A-3E can perform as a thermostat and relay switch 600. The thermostat and relay switch 600 consists of a wire embedded in shape memory polymer to provide the coil 200. The end of the coil 200 is oriented such that it moves the contacts 600*a* of the thermostat and relay switch 600. When current passes through the wire, it moves the contacts 600*a* of the thermostat and relay switch 600. Referring now to FIG. 6B, no current through wire of the coil 200 it moves the contacts 600*a* of the thermostat and relay switch 600. Referring now to FIG. 5A, current running through wire of the coil 200 causes contracting of the coil 200 and it moves the contacts 600*a* of the thermostat and relay switch 600.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A micropump device, comprising:

a micropump body, a moveable cylinder in said micropump body, a coil made from a wire embedded in shape memory polymer to provide said coil, wherein said coil includes a first loop of said wire embedded in shape memory polymer wherein said first loop is in a first loop shape, a second loop of said wire embedded in shape memory polymer wherein said second loop is in a second loop shape, wherein said second loop is adjacent said first loop, and a power source that provides a current to said coil and said current causes contracting of said coil, wherein said power source is turned on and off causing said current to said coil to be turned on and off resulting in said current alternatingly causing contracting of said coil moving said moveable cylinder in said micropump body for operating the micropump device.

* * * * *